United States Patent [19]

Monache et al.

[11] Patent Number: 5,059,624

[45] Date of Patent: Oct. 22, 1991

[54] GUANIDINE DERIVATIVES HAVING HYPOTENSIVE ACTIVITY, COMPOSITION CONTAINING THEM AND PROCESS FOR OBTAINING THEM

[75] Inventors: Giuliano D. Monache; Franco D. Monache; Marco Carmignani, all of Rome, Italy; Stella C. Bonnevaux, Montevideo, Uruguay; Romulo Espinal, Valencia, Venezuela; Carlo De Luca, Bracciano; Bruno Botta, Manziana, both of Italy

[73] Assignee: Consiglio Nazionale Delle Ricerche, Rome, Italy

[21] Appl. No.: 315,107

[22] Filed: Feb. 24, 1989

[30] Foreign Application Priority Data

Feb. 24, 1988 [IT] Italy ................................ 47665 A/88

[51] Int. Cl.$^5$ ............................................ A01N 37/18
[52] U.S. Cl. .................................... 514/616; 514/613; 514/617; 514/622; 514/634; 514/635; 564/156; 564/157; 564/170; 564/171; 564/236; 564/237; 564/240; 564/241; 424/195.1; 560/55; 560/148; 560/159
[58] Field of Search ...................... 424/195.1; 514/551, 514/634, 635, 616, 613, 617, 622, 631; 564/170, 171, 236, 237, 241, 157, 156, 240

[56] References Cited

U.S. PATENT DOCUMENTS

| | | | |
|---|---|---|---|
| 3,201,459 | 8/1965 | Coda et al. | 564/240 |
| 3,202,710 | 8/1965 | Bolger | 564/240 |
| 3,332,988 | 7/1967 | Mull | 564/237 |
| 3,459,792 | 8/1969 | Mull | 564/237 |
| 4,851,441 | 7/1989 | Higa et al. | 514/551 |

OTHER PUBLICATIONS

Heesing et al. CA:671679 vol. 72, 1970 (abstract only).
Evans Medical Ltd. CA: 614e, vol. 64, 1966 (abstract only).

*Primary Examiner*—Glennon H. Hollrah
*Assistant Examiner*—Shailendra Kumar
*Attorney, Agent, or Firm*—Pollock, Vande Sande & Priddy

[57] ABSTRACT

Guanidine derivatives of the following formulas (1) and (2):

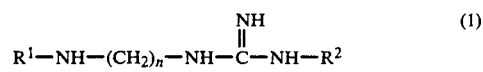

wherein:
$R^1$ is hydrogen or optionally substituted cinnamoyl,
$R^2$ is hydrogen, alkyl or alkenyl, with the proviso that $R^1$ and $R^2$ cannot be both hydrogen,
n is an integer from 1 to 8, or:

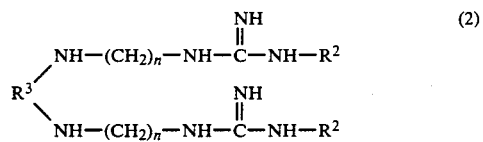

wherein
$R^3$ is truxinoyl or a truxilloyl each optionally substituted, and
$R^2$ and n are as defined above;

pharmaceutical compositions containing such compounds and a process for their extraction and purification from plant material, in particular from *Verbesina caracasana*.

8 Claims, No Drawings

GUANIDINE DERIVATIVES HAVING HYPOTENSIVE ACTIVITY, COMPOSITION CONTAINING THEM AND PROCESS FOR OBTAINING THEM

The present invention relates to new guanidine derivatives having hypotensive activity, to the compositions containing the same and to a process for their production, consisting in extracting and purifying said products from plant materials. More particularly, this invention relates to novel compounds whose formula comprises the guanidine group, which compounds show a remarkable hypotensive activity.

In the field of therapeutical treatment of hypertension some active principles of the class of guanidines are already known, the most widespread among them being guanetidine, whose molecule is made up of an 8-membered heterocyclic saturated ring, containing one nitrogen atom, which nitrogen atom is linked to a chain having two methylene groups and ending in the guanidine group.

Other guanidine compounds known as antihypertensive agents are guanfacine and guanabenz, both characterized by a structure having a benzene ring substituted with two chlorine atoms at one end and having the guanidine group at the other end.

However, all such products are obtained by chemical synthesis, and it is well known to those who are skilled in the art that this feature gives generally higher risks of toxicity with respect to substances of natural origin, because of the possible presence in the final product of trace amounts of reagents, of intermediate compounds and/or reaction by-products. Moreover, it is also well known that drugs obtained by synthesis generally require production processes which are more expensive and more complex than drugs obtained from natural sources.

Accordingly, the object of the present invention is to provide guanidine compounds that show a hypotensive activity comparable to or higher than the activity of compounds already known, but that can be obtained from largely available natural sources through simple and economically convenient extraction and purification procedures.

Studies and experimentations carried out to that aim within the present invention resulted in the isolation of a series of guanidine compounds from the extract of a plant, the *Verbesina caracasana* (Compositae), which compounds showed a remarkable hypotensive activity. Although only the above-mentioned species has been investigated, it cannot be excluded that similar compounds (which are water soluble) can be found in other species of Verbesina, especially if the fact is considered that preceding phytochemical studies reported in the literature for such genus are in all cases limited to the examination of the liposoluble components.

Further to the newly isolated guanidine compounds, a number of structurally related compounds have been synthesized and tested, thereby resulting in the definition of a new class of guanidine derivatives showing remarkable hypotensive activity.

Accordingly, the present invention provides new guanidine derivatives having either of the following general formulas:

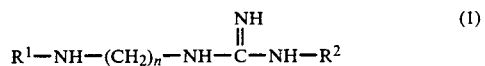

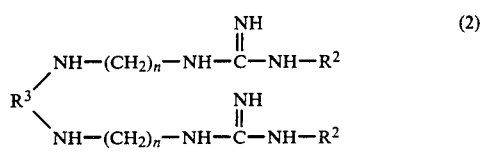

wherein:
$R^1$ is hydrogen or optionally substituted cinnamoyl, i.e.:

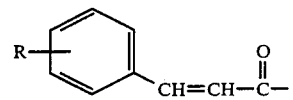

where R represents hydrogen or one or more substituents,
$R^2$ is hydrogen, alkyl or alkenyl, with the proviso that $R^1$ and $R^2$ cannot be both hydrogen, and
n is an integer from 1 to 8, and
$R^3$ is truxinoyl or truxilloyl, each optionally substituted, i.e., respectively:

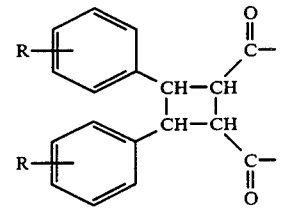

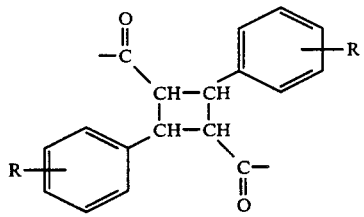

where R has the same meaning as above.

Preferably, the alkyl or alkenyl group $R^2$ has up to 5 carbon atoms; more preferably, $R^2$ is prenyl, i.e. 3-methyl-2-butenyl.

More specifically, the invention includes the following four compounds which have been isolated and identified in the extract of *Verbesina caracasana:*

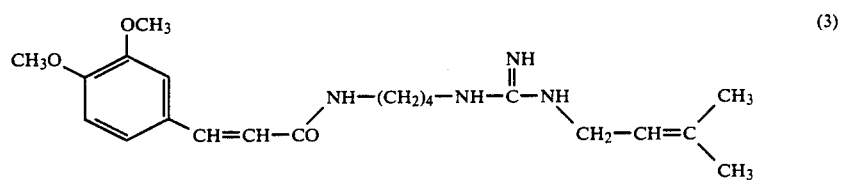

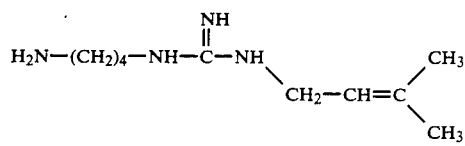

(4)

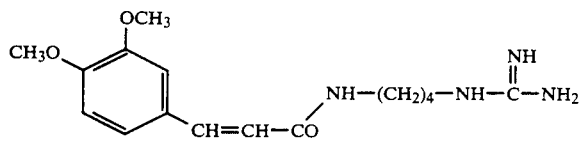

(5)

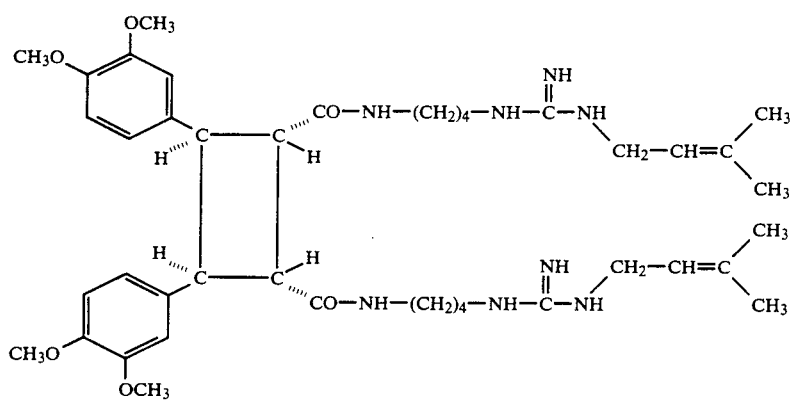

(6)

Compound (3) has been called guanido-I, and is comprised in the general formula (1) for $R^1$=3,4-dimethoxycinnamoyl, n=4 and $R^2$=prenyl; compound (4), called guanido-III, as a matter of practice is a prenylagmatine (agmatine, which is already known, is 4-(aminobutyl)-guanidine); compound (5) has been called guanido-V and it can be practically derived from guanido-I without the prenyl radical on the guanidine group; compound (6) comes within the general formula (2) when $R^3$ is bis(3,4-dimethoxy)βtruxinoyl, n is 4, $R^2$ is prenyl, and it has been called diguanido-II.

It can be easily recognized that compounds (4) and (5) (guanido-III and -V) are fragments of the molecule of the guanido-I, and that diguanido-II has a structure deriving from a dimerization of guanido-I through addition to the double bonds.

Chemical characterization of the preferred compounds of the present invention will be given further on in the example, and the pharmacological data proving the high hypotensive activity of said compounds will also be reported.

The invention also includes pharmaceutical compositions for treating hypertension containing, as the active ingredient, one of the guanidine compounds of the formulas (1) or (2), or a mixture of two or more of said compounds, or even an unfractionated extract of *Verbesina*, in particular of *Verbesina caracasana*.

The present invention further provides an extraction and purification process for obtaining the above-mentioned compounds from plant materials, said process being characterized in that it comprises the operations of:

a) treating the plant material, made into small pieces or ground, with an alcoholic solvent for extraction;
b) removing the solvent in vacuo;
c) distributing the extraction residue between ethyl acetate and water;
d) subjecting the water fraction to lyophilization (freezedrying).

Preferably, in order to increase the purity of the product, the raw lyophilized extract from the last above-mentioned operation is suspended again in an anhydrous alcoholic solvent and filtered, so as to remove any remaining insoluble material, which is made up mainly of inorganic salts; then the solvent is removed by evaporation, and a new, purified raw extract is obtained. In order to further increase the purity of such product, the preceding operation can be repeated a number of times with decreasing volumes of the alcoholic solvent.

To obtain a higher yield of the compounds of the invention it is also preferable to recover through water extraction the possible part of the active principle left behind in solution in the ethyl acetate employed in step c).

As an alternative to the process disclosed above, it is possible to substitute a water extraction at room temperature for the steps a), b) and c), with substantially similar yields.

The raw extract resulting from step d) (or the purified product obtained according to the preferred procedure) is then subjected to a process for separating the components on a silica column, eluting with chloroform containing increasing amounts of methanol; said separation can also be performed employing Sephadex LH-20 and eluting with methanol.

In addition to the extraction process proposed above, which by the moment represents a simple and economic way for producing the guanidine compounds of the invention, it is also possible to provide other production techniques, such as for instance biotechnological processes from plant cell cultures, seedlings, immobilized cells or even from microorganisms (bacteria, yeasts).

Furthermore, the compounds of the invention may be prepared by chemical synthesis, by adapting methods already known, for instance as described in some of the following examples.

The present invention will be now disclosed, for illustrative but not for limitative purposes, with particular reference to some of its preferred embodiments, in the following examples.

EXAMPLE 1

Extraction procedure 10 kg of *Verbesina caracasana* (the whole fresh plant) collected near Valencia (Venezuela, Carabobo State) is grossy made into pieces and extracted by a continuous process (with a Soxhlet apparatus) for 15-20 hours with methanol. After removing the solvent in vacuo at 30-35° C., the residue (about 700 g) is distributed between ethyl acetate and water.

Such operation allows to eliminate a large part of undesired compounds (triterpenes, chlorophyll, and so on), which are left behind in the organic solvent. The main part of the desired compounds are separated in the water phase (fraction A). The remaining part of the active ingredients, extracted by ethyl acetate, is recovered by a further water extraction (fraction B). The water soluble portion (A+B) is concentrated in vacuo at 35-40° C. and lyophilized, giving a raw extract C (of about 380-400 g).

By substituting ethanol for methanol in the continuous extraction process (Soxhlet), or by extracting the plant with water at room temperature, substantially the same yields of the raw extract C are obtained.

Then, the raw extract C is suspended in absolute methanol or ethanol and filtered. Such operation, as already illustrated above, results in the elimination of a large part of inorganic salts (about 70 g), the presence of which would complicate the subsequent chromatographic separation process. A further evaporation of the alcohol soluble portion gives the raw extract (310-330 g). By repeating the operation with lower amounts of alcohol further amounts of salts can be removed.

EXAMPLE 2

Separation of components

Method A

A portion (about 80 g) of the extract D mentioned in the preceding example (it is to be pointed out, however, that the process can be also carried out on the raw extract C, even though the results obtained are not as satisfying) is dissolved/suspended in methanol and then it is absorbed on 100-150 g of silica. After removing the solvent, the mixture (silica +the raw extract D) is put at the top of a silica column prepared in chloroform. Eluting with 3.5 l of chloroform allows elimination of trace amounts of chlorophyll and other undersired compounds. Repeated eluting with chloroform mixtures containing increasing amounts (10-50%) of methanol gives the compounds diguanido-II, guanido-I,—III, -IV (unidentified) -V, agmatine and galegine (a compound which is already known and definable as prenylguanidine) as relatively pure substance. The approximate amounts of each compound which are obtained from about 80 g of the raw extract D are the following: guanido-I: 3-6 g; diguanido-II: 3-5 g; guanido-III: 0.5-1 g; guanido-IV: 1-2 g; guanido-V: 0.5-1 g; agmatine: 0.5-1 g.

The yield of each component depends on various factors such as for instance the harvesting time or the ways by which the raw extract D is prepared. It has been observed that harvesting the plants at the end of summer gives higher yields of diguanido-II with less amounts of guanido-I, probably owing to photodimerization of the latter. Similarly, prolonged heating or the employment of higher temperatures during evaporation result in higher yields of guanido-III and -IV, again with less amounts of guanido-I, probably owing to partial hydrolysis of the latter.

It is to be observed that, if the above-mentioned compounds are to be obtained in their pure form, it is necessary to perform a further chromatographic purification.

Method B

The raw extract of *Verbesina caracasana* has also been subjected to a preliminary purification process by Sephadex LH-20. By eluting with methanol a partial separation into three fractions according to the molecular weight can be obtained. The first fraction contains the compound diguanido-II, while the second fraction consists of a mixture of the compounds guanido-I, -IV and -V, and the third fraction is made up of a mixture of guanido-III, agmatine and galegine. The purification by a Sephadex LH-20 column was also employed to obtain the individual components in their pure form.

EXAMPLE 3

Chemical characterization of guanido-I

The structure attributed according to formula (3) has been determined on the basis of spectroscopic data and of the results obtained by alkaline hydrolysis Mass spectrum at high resolving power: $M^+388.2472$; calculated for $C_{21}H_{32}O_3N_4$, $M^+388.2474$. Mass spectrum: 388 (6), 387 (5), 373 (3), 302 (5), 30i (12), 207 (45), 206 (32), 191 (100), 163 (21), 133 (11), 91 (45).

UV spectrum (MeOH), 291 and 330 nm. $^1H$ NMR spectrum ($D_2O$; cis-form predominant), $\delta$,7.15-6.95 (3H, m, H-2, H-5, H-6); 6.78 (1H, t, J=7 Hz, CH=),6.52 (1H, d, J=13 Hz, $H_\alpha$). 5.98 (1H, d, J=13 Hz, $H_\beta$), 5.18 (1H, broad t, J=7 Hz, HC=C), 3.85 and 3.82 (3H each. 2S, 2x OMe), 3.74 (2H, t, J=7 Hz, $CH_2$), 3.5-2.9 (4H, m, 2x $CH_2$), 1.76 (6H, broad s, 2x Me), 1.6-1.3 (4H, m, 2x $CH_2$).

$^1H$ NMR spectrum ($CDCl_3$—$CD_3OD$, 3-1; 1/1 mixture of the cis-and trans-forms), $\delta$, 7.55-6.90 (3H, m, H-2, H-5, H-6), 7.52 (1/2H, d, J=16 Hz, trans H-$\alpha$, 6.71 (1/2H, d, J=13 Hz, cis H-$\alpha$ 6.62 (1/2H, d, J=16 Hz, trans H-$\beta$, 5.96 (1/2H, d, J=13 Hz, cis H-$\beta$, 5.25 (1H, broad t, J=7 Hz, CH=), 3.75 (6H, s, 2x OMe), 3.73 (2H, d, J=7 Hz), 3.5-3.0 (4H, m, 2x $CH_2$), 1.75 (6H, broad s, 2x Me), 1.75-1.35 (4H, m, 2x $CH_2$).

$^{13}C$ NMR spectrum ($CD_3OD$), $\delta$, 170.1, 169.1 (CO), 157.4 (C=NH), 152.3, 150.8 (C-3, C-4), 141.7, 140,8, (C-$\alpha$), 139, 138.2 (C-1), 129.3 (C=), 124.6, 122.6 (C-6), 123.3 (CH=), 119.7, 119.4 (C-$\beta$), 114.3, 112.9 (C-2), 112.4, 111.6 (C-2), 56.5 (2x OMe), 42.3, 40.5, 39.8 (3x N-$CH_2$), 27.7, 27.2 (2x $CH_2$), 25.8, 18.1 (2x $CH_3$).

The compound (3) gave by hydrolysis (with 0.25N $Ba(OH)_2$ under reflux for 4 hours) a mixture of the cis- and trans-3,4-dimethoxycinnamic acid and the following compounds (7)-(9) reported hereinbelow:

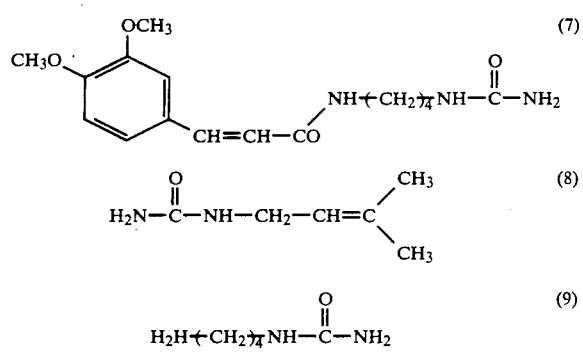

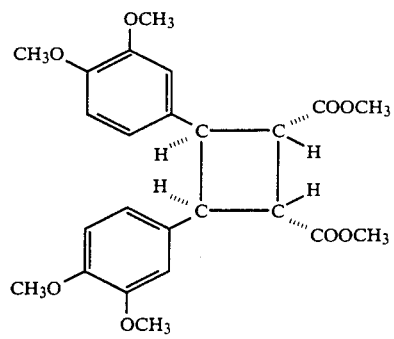

Compound (7): melting point 200–1° C. $C_{16}H_{23}N_3O_4$: calculated 321.1688; $M^+$, 321.1673 (HR MS). The results of the UV, IR, $^1H$ NMR spectra as well as the mass spectrum fragmentation are in agreement with the structure.

Compound (9): melting point 102–3° C.; $C_5H_{13}N_3O$ (M.W. 131), $[M+H]^+$ 132 (MS, chemical ionization); $^{13}C$ NMR ($D_2O$) 168 (C=O), 39.9 and 39.8 (N-$CH_2\times 2$), 26.8 and 24.8 ($CH_2\times 2$); $^1H$ NMR and mass spectrum fragmentation agree with the structure.

EXAMPLE 4

Chemical characterization of diguanido-II

The structure assigned to the compound according to the formula (6) has been determined on the basis of spectroscopic data and of the results of alkaline and acid hydrolyses.

$C_{42}H_{64}N_8O_6$ (M.W. 776), mass spectrum (FAB), 777 $[M+1]^+$ (100), 761 (4), 747 (6), 709 (11), 667 (2), 650 (3), 636 (5), 622 (2), 596 (3), 579 (25), 551 (11), 389 (46), 191 (57). $^1H$ NMR spectrum ($CDCl_3$–$CD_3OD$, 3-1): δ, 7.3 (2×1H, s), 6.7–6.4 (2x 2H, m), 5.2 (2x CH, broad t), 4.4–3.5 (2x 8H, m), 3.73 (2x 3H, s), 3.62 (2x 3H, s), 3.3–3.0 (2x 4H, m), 1.70 (2x 6H, broad s). $^{13}C$ NMR spectrum ($CD_3OD$): δ, 174.8 (CO), 157.8 (C=NH), 150.4, 149.4 (C-3, C-4), 134.3 (C=), 130.9 (C-1), 122.0, 120.0 (C-6, CH=), 114.2, 113.0 (C-5, C-2), 57.0, 56.9 (2x OMe), 46.4, 45.6 (2x CH), 42.9, 41.1, 40.4 (3x N—$CH_2$), 28.1, 27.8 (2x $CH_2$), 26.4, 18.7 (2x $CH_3$).

The compound (6) gave by hydrolysis (with 2N NaOH, 5 days at room temperature) the compounds (4) (guanido-III), (8) and (10), the last one reported hereinbelow:

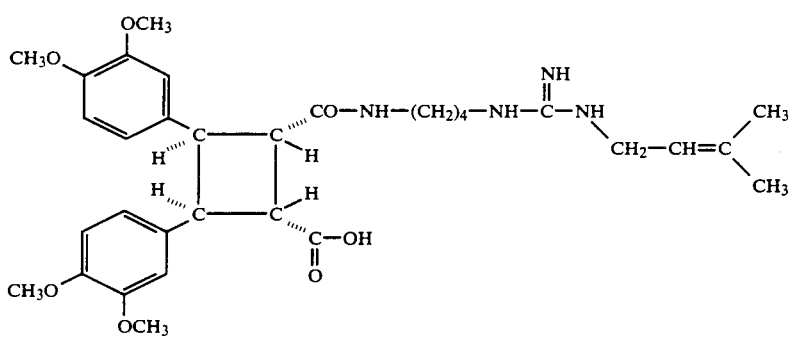

Compound (10): $^1H$ NMR ($CDCl_3$–$CD_3OD$); δ, 6.85 (2x 2H, broad s), 6.45 (2x 1H, broad s), 5.2 (1x C=, broad t), 4.4–4.2 (2x CH, m), 3.9–2.8 (12H, m), 3.70 (2x OMe, s), 3.6 (2x OMe, s), 1.75 (6H, broad s).

$^{13}C$ NMR ($CDCl_3$–$CD_3OD$); δ, 179.0, 173.7 (CO), 158 (C=NH), 148.0, 147.9, 146.8, 146.6 (C-3, C-4), 138.3 (C=), 133.2, 132.8, (C-1), 119.7, 119.6, 118.5 (C-6, C=) 118.8, 111.5, 1110.5, 110.4 (C-5, C-2), 55.3, 55.2 (4x OMe), 46.7, 45.3, 44.3, 40.7 (4x CH), 42.9, 39.1, 38.1 (3x N—$CH_2$), 26.2, 24.8 (2x $CH_2$), 25, 17.3 (2x $CH_3$).

The compound (10) gave by acid hydrolysis (with HCl 2N in MeOH, under reflux for 3 hours) the following compound (11):

Compound (11): $^1H$ NMR ($CDCl_3$); δ, 6.67 (2x 1H, d), 6.57 (2x 1H, d), 6.22 (2x 1H, d), 4.30 (2x 1H, d), 3.79 (2x 3H, s), 3.77 (2x 1H, d), 3.75 (2x 3H, s), 3.63 (2x 3H, s).

$^{13}C$ RMN (acetone-$d_6$); δ, 173.7 (C=0), 151.4, 148.8 (C-3', C-4'), 132.6 (C-1'), 120.8 (C-6'), 113.2 (C-2'), 112.0 (C-5'), 55.91, 55.89 (OMe), 52.1 (COOMe), 45.6 (C-β), 43.9 (C-α) Mass spectrum: $M^+$ 444, m/z 300.

EXAMPLE 5

Chemical characterization of guanido-III

The structure assigned to the compound according to formula (4) has been determined on the basis of spectroscopic data and of the results of alkaline hydrolysis.

$C_{10}H_{22}N_4$ (M.W. 198), mass spectrum (FAB) 199 $[M+1]^+$.

$^1H$ NMR spectrum ($CDCl_3$–$CD_3OD$, 3-1): δ, 5.2 (1H, m, =CH), 4.0–3.60 (10H, m, 5x $CH_2$), 1.75 (6H, s, 2x $CH_3$).

$^{13}C$ spectrum (4·AcOH) ($CD_3OD$): δ, 181 (CD, AcOH) 155.6 (C=NH), 139 (C=), 117.5 (CH=), 40.5, 39.1, 39.0 (3x N—$CH_2$), 25.1, 24.1 (2x $CH_2$), 24.7 ($CH_3$, AcOH), 23.3, 17.1 (2x $CH_3$).

The compound (4) gave by hydrolysis (with 0.25N Na(OH)$_2$, under reflux for 2 hours) the compounds (8) and (9) (already disclosed in Example 3) and urea.

EXAMPLE 6

Chemical characterization of guanido-V

The structure assigned to the compound according to formula (5) has been determined on the basis of spectroscopic data and of the results of mild hydrolysis.

$C_{16}H_{24}N_4O_3$ (M.W. 320), mass spectrum (FAB) 321[M+1]+·

$^1$H NMR (CD$_3$OD); δ, 7.5 (H-2), 7.2 (H-6), 7.0 (H-5), 6.8 (H$_\alpha$), 6.1 (H$_\beta$), 4.0 (2x OMe), 3.55–3.3 (2x CH$_2$), 1.9–1.7 (2x CH$_2$).

$^{13}$C NMR (CD$_3$OD): δ, 169.2 (CO), 157 (C=NH), 150, 148.9 (C-3, C-4), 141.3 (C-α), 128.7 (C-1), 122.2 (C-β), 121.9 (C-6), 113.2, 111.3 (C-5, C-2), 55.4, 55.3 (2x OMe), 39.8, 39 (2x N—CH$_2$), 26.8, 26.3 (2x CH$_2$).

The compound (5) gave by hydrolysis (with 0.25 N Na(OH)$_2$, under reflux for 2 hours) a mixture of the cis- and trans-3,4-dimethoxycinnamic acids and the compounds (7) and (9) already disclosed in example 3.

EXAMPLE 7

Chemical synthesis of guanido-V, i.e. 4-[(3,4-dimethoxycinnamoyl)amino]butylguanidine 5.8 g of di-tert-butyl dicarbonate (12) is added to 2.5 g of S-methoxythiourea H$_2$SO$_4$ (i.e. 2-methyl-2-thiopseudourea sulfate) (13) and the mixture is left in a two-phase CH$_2$Cl$_2$—NaHCO$_3$ system (50 ml + 50 ml, respectively) for two days under stirring, so as to achieve the tert-butoxycarbonylation (t-BOC) of the two amine groups.

The scheme of reation is as follows:

$$H_2N-\overset{NH}{\overset{\|}{C}}-SCH_3 + O[COO-C(CH_3)_3]_2 \longrightarrow$$
(13)                             (12)

$$H_3CS-\overset{N-COO-C(CH_3)_3}{\overset{\|}{C}}-NH-COO-C(CH_3)_3$$
(14)

After separation of the two phases, the water fraction is further extracted with CH$_2$Cl$_2$. After purification, 3.4 g of compound (14) is obtained.

200 mg of compound (14) is reacted with 63 mg of 1,4-diaminobutane (tethramethylenediamine) (15) in 5 ml THF and 0.i ml H$_2$O. The reaction mixture is heated to 50° C for 3 hours, so that the following reaction occurs:

$$H_2N-(CH_2)_4-NH_2 + H_3CS-\overset{N-t-BOC}{\overset{\|}{C}}-NH-t-BOC \longrightarrow$$
(15)                         (14)

$$H_2N-(CH_2)_4-NH-\overset{N-t-BOC}{\overset{\|}{C}}-NH-t-BOC$$
(16)

After evaporation of the solvent, the residue is washed with NaHCO$_3$ 5% and extracted with CHCl$_3$. After purification on silica 120 mg of compound (16) is obtained.

The compound (16) (500 mg) is reacted with 370 mg of 3,4-methoxycinnamoylchloride (17) in THF-DMF (5 ml - 5 ml) for 16 hours at room temperature, according to the following scheme:

[Structure (17): 3,4-dimethoxycinnamoyl chloride with OCH$_3$ groups, CH=CH—COCl]
(17)

$$H_2N(CH_2)_4NH-\overset{N-t-BOC}{\overset{\|}{C}}-NH-t-BOC \longrightarrow$$
(16)

[Structure (18): 3,4-dimethoxycinnamoyl-amide with CH=CH—CO—NH(CH$_2$)$_4$NH—C(=N-t-BOC)—NH-t-BOC]
(18)

After purification on silica, by eluting with ethylacetate-hexane (10–90), 300 mg of compound (18) is obtained.

Thereafter, 1,5 ml of TFA is added to 23 mg of compound (18) and the mixture is stirred at room temperature for 43 minutes. Then, the mixture is dried over P$_2$O$_5$ and purified on Sephadex LH-20, by eluting with methanol, thus obtaining 12 mg of guanido-V, i.e. compound (5).

EXAMPLE 8

Chemical synthesis of guanido-I, i.e. 1-{4-(3-4-dimethoxycinnamoyl)amino/butyl)}-3-prenylguanidine 1,5 g of prenyl bromide (γ,γ'-dimethylallylbromide) (19) is added to a solution containing i g of guanido-V (obtained, f.i., according to the procedure of Example 7), i.e. compound (5), in 10 ml of anhydrous THF, and a catalytically effective amount of N,N'-dimethylaminopyridine.

The reaction mixture is kept under stirring at room temperature for 6 hours. After purification, 750 mg of compound (3), i.e. guanido-I, is obtained.

The scheme of the reaction is the following:

[Structure (5): 3,4-dimethoxycinnamoyl derivative CH=CH—CO—NH—(CH$_2$)$_4$—NH—C(=NH)—NH$_2$]  + Br—CH$_2$—CH=C(CH$_3$)$_2$
(5)                                               (19)

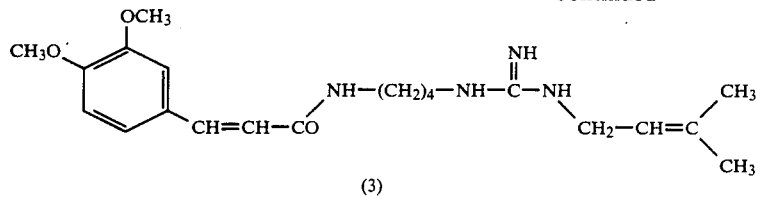

(3)

EXAMPLE 9

Chemical synthesis of 3-[(3,4-dimethoxy 1)amino]propylguanidine

The same procedure as in example 7 is followed, with the exception that i,3-diaminopropane is employed instead of compound (15) (1,4-diaminobutane).

EXAMPLE 10

Chemical synthesis of 1-{3-[(3,4-dimethoxycinnamoyl)amino]propyl}-3-prenylguanidine In the same manner as described in Example 8, the title compound is obtained by alkylation of the compound of Example 9.

EXAMPLE 11

Chemical synthesis of 6-[(3,4-dimethoxycinnamoyl)amino]hexylguanidine

The procedure described in Example 7 is repeated employing hexamethylenediamine (16-hexanediamine) instead of compound (15).

EXAMPLE 12

Chemical synthesis of 1-{6-[(3,4-dimethoxycinnamoyl)amino]hexyl}-3-prenylguanidine The procedure described in Example 8 is repeated starting from the compound of Example 11.

Activity of the raw extract

In order to check the activity of the raw extract of *Verbesina carasana*, a 0.9 % sodium chloride solution of such extract was administered by l.v. "rapid" route to dogs under general chloralose anaesthesia. The responses induced at the level of (mean) systemic arterial pressure, respiratory frequency and following bilateral carotid occlusion were evaluated. The results, which are reported in the following Table 1, put into evidence that the hypotensive activity is proportional to the dose, the maximum value of the hypotensive activity being reached at the dose of 2 mg/kg.

TABLE 1

| NUMBER OF ANIMALS | DOSE (mg/kg) | BP (mmHg) | $-\Delta p$ (mmHg) | $-\Delta p$ (%) |
|---|---|---|---|---|
| 5 | 0.5 | 162 ± 10 | 23 ± 10 | 13 |
| 6 | 1 | 154 ± 8 | 48 ± 18 | 31 |
| 6 | 2 | 159 ± 7 | 92 ± 14 | 58 |
| 4 | 4 | 155 ± 6 | 85 ± 8 | 55 |

BP = aterial basal pressure
$-\Delta p$ = decrease in pressure

The administration of the extract to mice causes hair erection, stimulation, and subsequently death from respiratory block.

Activity of the compounds of the invention

Guanido-I

In order to test its activity, guanido-I (compound (3)), dissolved in a 0.9 % sodium chloride solution, was administered through i.v. "rapid" route to male Wistar rats anaesthetised with 10% ethyl urethan (1 ml/hg).

The parameters estimated and reported in the following Table 2 for various doses of guanido-I administered are: changes in the systolic and diastolic systemic arterial pressure ($\Delta AP$), changes in the heart rate ($\Delta HR$), in the maximum rate of increase in the left ventricular isovolumetric pressure ($\Delta dp/dt$) as an index of cardiac inotropism and changes in the respiratory frequency ($\Delta RF$)

TABLE 2

| No. of animals | Dose (μg/kg) | $\Delta AP$ (mmHg) SYST | $\Delta AP$ (mmHg) DIAST | $\Delta HR$ (beats/min) | $\Delta dp/dt$ (mmHg/sec) | $\Delta RF$ (acts/min) |
|---|---|---|---|---|---|---|
| 6 | 50 | −4 ± 2 | −5 ± 1 | +8 ± 3 | +52 ± 8 | +6 ± 2 |
| 6 | 100 | −6 ± 2 | −6 ± 2 | +10 ± 1 | +141 ± 25 | +9 ± 4 |
| 6 | 200 | −11 ± 3 | −10 ± 2 | +13 ± 2 | +1284 ± 78 | +12 ± 2 |
| 6 | 400 | −15 ± 4 | −14 ± 3 | +14 ± 5 | +1712 ± 107 | +16 ± 3 |
| 12 | 800 | −17 ± 3 | −15 ± 3 | +18 ± 4 | +2140 ± 263 | +25 ± 6 |
| 12 | 1600 | −21 ± 6 | −18 ± 4 | +22 ± 3 | +2996 ± 104 | +23 ± 9 |
| 12 | 3200 | −25 ± 5 | −29 ± 4 | +25 ± 8 | +2984 ± 362 | +26 ± 7 |
| 12 | 6400 | −34 ± 4 | −29 ± 2 | +20 ± 4 | +3074 ± 441 | +29 ± 5 |

The results reported in Table 2 point out that guanido-I lowers the value of AP according to a linear dependence on the dose, whereas it causes an increase in the values of HR, dp/dt and RF. In the case of the tidal volume (TV), a linear increase has been observed with the doses of guanido-I administered. Such cardiovascular effects do not seem to be correlated to significative actions of the active ingredient at the level of the peripheral adrenergic receptors ($\alpha_1$-$\alpha_2$; $\beta_1$-$\beta_2$) rather to central neurogenic mechanisms (as, for instance, it can be put into evidence by experiments of spinalization and of ganglionic block) and to peripheral-effectorial mechanisms, for example on the processes of muscular contractility, in myocardium cells and vascular myocells.

In particular, the heart rate (HR) increases at all doses tested owing to a direct effect (at the cardiac and/or central level) and to a reflection following arterial hypotension. Similar considerations also hold true for dp/dt, while the increase in the respiratory frequency (RF), correlated to the doses of the compound, and present at all doses tested, can be traced to a constant stimulation effect on the central respiratory centers.

The lethal dose 50 ($LD_{50}$) of guanido-I through i.p. route in mice turned out to be 57 mg±3.6 per kg.

Diguanido-II

In order to check its activity, diguanido-II was dissolved in a 0.9 % sodium chloride solution and administered through "rapid" i.v. route in male Wistar rats, under general anaesthesia obtained by means of 10% ethyl urethan (i ml/hg).

The results obtained with various doses of the compound are reported in Table 3, in which the changes in the aortic flow at the iliac bifurcation (/ AF) as well as the changes in the stroke volume (/ SV) are reported in addition to the parameters already illustrated above.

Table 4 also shows the percentage values corresponding to those shown in Table 3 and, in addition, it also shows the values of the percentage changes in the tidal volume ($\Delta$ TV).

As a matter of practice, the increase in RF and TV at lower doses can be ascribed to a central stimulation effect on the respiratory centers. A central effect of the compound is also acting in the case of cardiovascular responses. At higher doses, a depression effect occurs, on the contrary, on the respiratory centers, which effect is not related to the cardiovascular ones. Indeed, such effects are to be ascribed to a reduction of the peripheral vascular resistance.

The reduction of heart rate (HR), at all doses of the compound, cannot be ascribed to reflexion mechanisms (baroreceptorial mechanisms). Such reduction persists in the presence of a constant increase in dp/dt and of inversion of the AF, SV and RF responses. It is thus evident that bradycardia induced by the compound guanido-II can only be explained by central mechanisms, differently with respect to the effects developed by the guanido-I.

The lethal dose 50 ($LD_{50}$) of the diguanido-II through i.p. route in mice, turned out to be 7 mg±0.6 per kg.

Guanido-III, -IV, -V, agmatine and galegine

TABLE 3

| NO. OF ANIMALS | DOSE (μg/kg) | Δ AP (mmHg) SYST | Δ AP (mmHg) DIAST | Δ HR (beats/min) | Δ dp/dt (mmHg/sec) | Δ AF (ml/min) | Δ SV (μl) | Δ RF (acts/min) |
|---|---|---|---|---|---|---|---|---|
| 12 | 50 | +17.2 ± 2.4 | +9.8 ± 1.7 | −9 ± 3 | +1070 ± 90 | +18.8 ± 3.40 | +72.6 ± 5 | +5.3 ± 2.7 |
| 12 | 100 | +11.7 ± 2.5 | +10.2 ± 1.1 | −10 ± 1 | +1129 ± 82 | +10.8 ± 1.20 | +19.8 ± 6 | +6.4 ± 2.93 |
| 12 | 200 | −14.4 ± 1.4 | −13.1 ± 1.8 | −13 ± 4 | +1369 ± 170 | −13.8 ± 4.20 | +23.1 ± 6 | +8.6 ± 3.7 |
| 18 | 400 | −19.8 ± 1.9 | −17.0 ± 1.4 | −16 ± 5 | +2615 ± 181 | −14.3 ± 5.7 | −46.2 ± 4 | −3.1 ± 0.9 |
| 18 | 800 | −30.0 ± 3.6 | −31.2 ± 3.1 | −16 ± 5.5 | +3282 ± 269 | −25.0 ± 6.1 | −85.8 ± 9 | −14.6 ± 4.3 |
| 18 | 1600 | −41.1 ± 5.3 | −43.4 ± 6.8 | −30 ± 6 | +3676 ± 264 | −36.1 ± 4.8 | −97.4 ± 8 | −61 ± 8.9 |
| 18 | 3200 | −47.8 ± 6.5 | −53.0 ± 4.2 | −41 ± 8 | +4708 ± 430 | −41.0 ± 6.9 | −117.2 ± 8 | −67 ± 2.9 |

TABLE 4

| No. OF ANIMALS | DOSE (μg/kg) | Δ AP % SYST | Δ AP % DIAST | Δ HR % | Δ dp/dt % | Δ AF % | Δ SV % | Δ RF % | Δ TV % |
|---|---|---|---|---|---|---|---|---|---|
| 12 | 50 | +15.0 ± 2.7 | +11.0 ± 1.7 | −3 ± 1 | +17 ± 4 | +43 ± 3 | +61 ± 5 | +6 ± 3 | +13 ± 3 |
| 12 | 100 | +10.0 ± 2.6 | +11.0 ± 1.1 | −3 ± 1 | +18 ± 1 | +25 ± 1 | +17 ± 6 | +7 ± 3 | +4 ± 1 |
| 12 | 200 | −13.0 ± 1.4 | −9.0 ± 1.8 | −4 ± 0.3 | +21 ± 4 | −32 ± 4 | +19 ± 6 | +9 ± 4 | +3 ± 2 |
| 18 | 400 | −18.0 ± 1.9 | −18.0 ± 1.4 | −5 ± 2 | +41 ± 5 | −33 ± 6 | −39 ± 4 | −3 ± 1 | −51 ± 7 |
| 18 | 800 | −27.0 ± 3.6 | −34.0 ± 3.1 | −5 ± 2 | +51 ± 7 | −57 ± 6 | −72 ± 9 | −15 ± 4 | −93 ± 8 |
| 18 | 1600 | −36.0 ± 5.3 | −47.0 ± 6.8 | −9 ± 3 | +57 ± 6 | −83 ± 5 | −82 ± 8 | −63 ± 9 | −98 ± 5 |
| 18 | 3200 | −42.0 ± 6.5 | −58.0 ± 4.2 | −12 ± 3 | +73 ± 9 | −94 ± 7 | −98 ± 8 | −70 ± 3 | −100 |

The compound diguanido-II gives biphasic effects on AP, AF, RF and TV: an increase in such parameters at doses between 50 and 100 μg/kg (AP, AF) or 50 and 200 μg/kg (SV), RF and TV), and a decrease in the same parameters a higher doses (up to 3,200 μg/kg).

Previous treatment with diguanido-II decreased the cardiovascular responses induced by hypertensive doses of nor-adrenaline and of adrenaline, and it increased the cardiovascular responses to administration, through i.v. route, of acetylcholine and isoproterenol, according to a linear law with respect to the doses of the agonists in question.

Previous treatment with Hexameton (gangliopegic) caused an increase in the cardiovascular responses to diguanido-II as mentioned above, whereas vagotonism was not followed by any modification in the response to diguanido-II.

Reserpinization, spinalization and previous treatment with alpha-blocking agents were not efficient in modifying cardiovascular and respiratory responses to diguanido-II.

The active ingredients called guanido-III, -IV, -V, as well as agmatine and galegine, were also tested, after having been administered through "rapid" i.v. route in male Wistar rats (weighing average 280±5 g) under general anaesthesia obtained by means of 10% ethyl uretan (1 ml/hg, i.p.). The general experimental conditions were exactly the same as previously mentioned for guanido-I and diguanido-II, so that the cardiovascular and respiratory effects could be compared.

The parameters measured are as follows: systolic and diastolic systemic arterial pressure (AP), heart rate (HR), maximum rate of increase in the left ventricular isovolumetric pressure (dp/dt), respiratory frequency (RF) and tidal volume (TV). The doses (in μg/kg body weight, referred to the active substance) varied from 50 μg/kg to 6,400 μg/kg (ratio = 2.0); in some cases higher does have been employed.

The experimental data relevant to guanido-III, guanido-IV, guanido-V, agmatine and galegine are shown respectively in Tables 5 through 9.

TABLE 5

| Dose (μg/kg) | Δ AP (mmHg) SYST | Δ AP (mmHg) DIAST | Δ HR (beats/min) | Δ dp/dt (mmHg/sec) | Δ RF (%) | Δ TV (%) |
|---|---|---|---|---|---|---|
| 200 | −2 ± 0.3 | −2 ± 0.2 | 0 | +214 ± 20 | +7 ± 4 | +9 ± 2 |
| 400 | −3.5 ± 1.5 | −2 ± 0.6 | 0 | +321 ± 17 | +7 ± 3 | +17 ± 6 |
| 800 | −11 ± 1 | −13 ± 4 | −15 ± 3 | +1356 ± 428 | +10 ± 4 | +33 ± 9 |
| 1600 | −13 ± 2 | −21 ± 4 | −23 ± 10 | +2157 ± 655 | +18 ± 3 | +21 ± 7 |
| 3200 | −36 ± 7 | −36 ± 6 | −26 ± 8 | +2640 ± 634 | −42 ± 9 | −73 ± 18 |
| 6400 | −112 ± 3 | −85 ± 3 | −310 ± 25 | −5422 ± 514 | −100 | −100 |

TABLE 6

| Dose (μg/kg) | Δ AP (mmHg) SYST | Δ AP (mmHg) DIAST | Δ HR (beats/min) | Δ dp/dt (mmHg/sec) | Δ RF (%) | Δ TV (%) |
|---|---|---|---|---|---|---|
| 200 | −5 ± 2 | −5 ± 1 | −9 ± 4 | +420 ± 72 | +40 ± 7 | +20 ± 5 |
| 400 | −9 ± 4 | −10 ± 3 | −11 ± 7 | +1070 ± 148 | +56 ± 5 | +39 ± 5 |
| 800 | −11 ± 4 | −13 ± 2 | −14 ± 7 | +1284 ± 201 | +16 ± 3 | +41 ± 8 |
| 1600 | −12 ± 5 | −16 ± 2 | −14 ± 5 | +1369 ± 322 | +2 ± 1 | +29 ± 4 |
| 3200 | −16 ± 3 | −24 ± 5 | −17 ± 8 | +2140 ± 240 | −23 ± 8 | −61 ± 5 |
| 6400 | −38 ± 6 | −41 ± 6 | −59 ± 11 | +2354 ± 177 | −82 ± 8 | −98 ± 2 |

TABLE 7

| Dose (μg/kg) | Δ AP (mmHg) SYST | Δ AP (mmHg) DIAST | Δ HR (beats/min) | Δ dp/dt (mmHg/sec) | Δ RF (%) | Δ TV (%) |
|---|---|---|---|---|---|---|
| 200 | 0 | 0 | 0 | −392 ± 21 | −7 ± 2 | −14 ± 4 |
| 400 | −4 ± 2 | −3 ± 1 | 0 | −384 ± 39 | −3 ± | −13 ± 2 |
| 800 | −5 ± 2 | −6 ± 2 | 0 | −430 ± 43 | −3 ± 2 | +12 ± 4 |
| 1600 | −8 ± 3 | −6 ± 2 | 0 | −642 ± 76 | −4 ± 1 | +11 ± 3 |
| 3200 | −10 ± 4 | −9 ± 3 | 0 | +684 ± 38 | +1 ± 1 | +20 ± 6 |
| 6400 | −11 ± 3 | −15 ± 4 | −14 ± 6 | +2354 ± 214 | +10 ± 4 | +22 ± 7 |
| 12800 | −23 ± 5 | −28 ± 4 | −49 ± 8 | +2996 ± 170 | +11 ± 3 | +74 ± 8 |
| 102400 | −24 ± 4 | −30 ± 5 | −67 ± 11 | +3040 ± 224 | +6 ± 4 | +79 ± 12 |

TABLE 8

| Dose (μg/kg) | Δ AP (mmHg) SYST | Δ AP (mmHg) DIAST | Δ HR (beats/min) | Δ dp/dt (mmHg/sec) | Δ RF (%) | Δ TV (%) |
|---|---|---|---|---|---|---|
| 200 | −5 ± 2 | −4 ± 1 | 0 | +300 ± 89 | +9 ± 3 | +3 ± 1 |
| 400 | −6 ± 1 | −6 ± 2 | 0 | +334 ± 54 | +11 ± 4 | +12 ± 4 |
| 800 | −8 ± 2 | −8 ± 2 | 0 | +947 ± 131 | +12 ± 4 | +14 ± 2 |
| 1600 | −9 ± 3 | −10 ± 1 | 0 | +981 ± 94 | +11 ± 2 | +25 ± 5 |
| 3200 | −9 ± 2 | −11 ± 2 | −7 ± 2 | +1356 ± 164 | +13 ± 4 | +27 ± 4 |
| 6400 | −11 ± 4 | −13 ± 4 | −13 ± 5 | +3351 ± 417 | +13 ± 5 | +30 ± 7 |
| 12800 | −12 ± 2 | −18 ± 5 | −17 ± 2 | +2568 ± 432 | +15 ± 2 | +31 ± 7 |
| 25600 | −12 ± 3 | −23 ± 4 | −17 ± 7 | +3565 ± 813 | +24 ± 4 | +33 ± 9 |
| 51200 | −15 ± 1 | −34 ± 6 | −22 ± 1 | +5491 ± 869 | +31 ± 7 | +35 ± 6 |

TABLE 9

| Dose (μg/kg) | Δ AP (mmHg) SYST | Δ AP (mmHg) DIAST | Δ HR (beats/min) | Δ dp/dt (mmHg/sec) | Δ RF (%) | Δ TV (%) |
|---|---|---|---|---|---|---|
| 50 | −18 ± 1 | −19 ± 3 | −32 ± 6 | +1498 ± 131 | +38 ± 4 | +43 ± 4 |
| 100 | −22 ± 2 | −28 ± 6 | −46 ± 7 | +1712 ± 90 | +68 ± 4 | +63 ± 5 |
| 200 | −23 ± 5 | −29 ± 5 | −94 ± 6 | +1797 ± 178 | +69 ± 7 | +64 ± 7 |
| 400 | −25 ± 6 | −26 ± 4 | −107 ± 4 | +2568 ± 314 | +76 ± 9 | +87 ± 9 |
| 800 | −27 ± 4 | −26 ± 4 | −106 ± 11 | +1926 ± 223 | +70 ± 8 | +31 ± 3 |
| 1600 | −22 ± 4 | −25 ± 4 | −85 ± 5 | +1724 ± 104 | +133 ± 14 | +55 ± 6 |
| 3200 | −22 ± 3 | −36 ± 4 | −98 ± 16 | +2996 ± 202 | +85 ± 6 | +40 ± 7 |
| 6400 | −18 ± 4 | −36 ± 2 | −42 ± 4 | +4494 ± 371 | +37 ± 11 | +29 ± 8 |
| 12800 | −22 ± 2.5 | −42 ± 3 | −15 ± 7 | +6420 ± 417 | +23 ± 7 | +25 ± 5 |
| 25600 | −19 ± 3 | −30 ± 9 | −21 ± 6 | +6471 ± 274 | −34 ± 12 | −57 ± 8 |
| 51200 | −80 ± 8 | −50 ± 7 | −298 ± 19 | −4708 ± 312 | −100 | −100 |

The compound guanido-III (Table 5) caused systolic and diastolic arterial hypotension (well evident starting from the dose of 800 μg/kg), bradycardia, increase of dp/dt (up to the dose of 3,200 μg/kg). increase of RF and TV (up to the dose of 1,600 μg/kg). RF and TV were lowered by a dose of 3,200 μg/kg; the dose of 6,400 μg/kg caused death of the tested animals: after a primary respiratory block, arterial hypotension followed, and then increasing reduction of HR and dp/dt; TV was interested prior than RF.

The compound guanido-IV (Table 6), tested in doses of 50–6,400 μg/kg. showed effects similar guanido-III, left ventricular isovolumetric pressure (Δdp/dt) are reported in the following Table 10.

TABLE 10

| COMPOUND UNDER TEST | Δ AP SYSTOLIC | (mmHg) DIASTOLIC | Δ HR (beats/min) | Δ dp/dt (mmHg/sec) |
|---|---|---|---|---|
| Guanetidine (5 mg/kg, i.v.) | −27 ± 5 | −19 ± 3 | −18 ± 6 | −863 ± 160 |
| Clonidine (25 mcg/kg, inf.) | −15 ± 4 | −9 ± 1 | −40 ± 8 | −871 ± 74 |
| Hexameton (2.5 mg/kg, i.v.) | −44 ± 2 | −34 ± 2 | −48 ± 9 | −4040 ± 812 |
| Reserpine (5 mg/kg, inf.) | −31 ± 6 | −24 ± 5 | −47 ± 9 | −1580 ± 134 |
| Papaverine (2 mg/kg, i.v.) | −23 ± 3 | −18 ± 3 | −21 ± 5 | −604 ± 102 |
| Adrenaline (0.125 mcg/kg, i.v.) | +10 ± 2 | −10 ± 0.5 | +9 ± 1 | +1562 ± 165 |
| (2 mcg/kg, i.v.) | +49 ± 3 | +39 ± 2 | +14 ± 2 | +3568 ± 330 |
| Noradrenaline (1 mcg/kg, i.v.) | +44 ± 3 | +31 ± 2 | +14 ± 4 | +4314 ± 415 |
| Bradykinin (0.75 mcg/kg, i.v.) | −18 ± 3 | −18 ± 4 | −11 ± 2 | −830 ± 124 |
| Histamine (5 mcg/kg, i.v.) | −30 ± 3 | −28 ± 3 | −7 ± 1 | −1314 ± 180 |
| 5-hydroxytryptamine (5 mcg/kg, i.v.) | −37 ± 3 | −39 ± 2 | −12 ± 3 | −1410 ± 167 | n = 10 Mean values ± M.S.E. Average weight of the animals: 284 ± 17 g.

though with a lower power: systolic and diastolic arterial hypotenslon, bradycardia, increase of dp/dt, RF and TV increased up to the dose of 1,600 μg/kg, and decreased for higher doses., the maximum dose tested did in no case result in death of the animal.

The compound guanido-V (Table 7) caused systolic and diastolic arterial hypotension, more evident from the dose of 3,200 μg/kg on; bradycardia was observed starting from the dose of 6,400 μg/kg, a slight reduction of dp/dt and RF appeared up to the highest doses; TV showed a similar trend.

The changes of AP and HR induced by agmatine (Table 8) were analogous to those induced by guanido-V., moreover, said active ingredient caused a constant increase in dp/dt, RF and TV.

Galegine (Table 9) caused systolic and diastolic arterial hypotension and bradycardla yet from the dose of 50 μg/kg with a constant increase of dp/dt, RF and TV. Only extremely high doses (25,600 and 51,200 ug/kg) caused a primary respiratory depression (reduction of RF and TV) and a subsequent arterial hypotension. bradycardia and decrease in the cardiac inotropism (dp/dt), with death of the tested animals.

Comparison with guanidine

The administration of guanidine (50–800 μg/kg) by "rapid" i.v. route, for comparison with the above-described active principles, did not cause in the rats under test significative alterations of RF, TV and HR., the other parameters showed slight changes for doses of guanidine of 6,400–1,2600 μg/kg. In the dose range of 50–800 μg/kg guanidine gave rise to slight and not significant hypotensive responses, and to a little reduction of dp/dt; for higher doses, guanidine caused, as far as systemic arterial pressure is concerned, biphasic responses of a slight entity (hypo-hypertension), coupled to a little increase in cardiac inotropism (dp/dt) and reduction of RF and TV, with no linear relationship with the doses employed.

Comparison with known active ingredients

In order to compare the activity of the compounds of the present invention to that of the products of the prior art, various doses of known anti-hypertensive, hypotensive and vasoactive drugs were administered to male Wistar rats under general anaesthesia by sodium thiopental (50 mg/kg, i.p.). The administration was effected through "rapid" i.v. route or through intravenous infusion (inf.) for a time of 5 minutes.

Responses in terms of changes in the systolic and diastoic systemic arterial pressure (ΔAP), of changes in heart rate (ΔHR) and in maximum increase in the rate of In table 10 th emaximum responses are shown. The dose of each product is referred to the base, and the volumes injected were of 100 mcl in case of i.v. administration and 0.170 mcl total (0.9% sodium chloride solution) in case of infusion. The various parameters were evaluated in the same way as in the preceding experiments.

As it can be observed from the data of table 10, the hypotensive, anti-hypertensive or vasoactive agents which are largely and predominantly employed as therapeutic agents for primary and secondary arterial hypertension and for vascular disorders of a multiform nature (guanitidine, clonidine, reserpine, papaverine and so on) are usually characterized by general "depressive" effects on the various haemodynamic parameters.

The availability of a drug like guanido-I, which is capable of giving hypotensive responses while increasing heart rate and inotropism as well as respiratory rate (and consequently also the peripheral arterial flow) appears to be a clearly advantageous therapeutical aid (because of a number of obvious considerations) with respect to the drugs mentioned above.

The compound diguanido-II, characterized by a higher pharmacological power as to hypotensive effect with respect to guanido-I, shows a constant stimulating action on the heart inotropism. Moreover, at all dose levels it does not cause any reflected tachycardia, which is a typical and undesired effect of most antihypertensive drugs commercially available (for instance: those having arterial vasodilating action, all alpha-blocking agents but the selective alpha$_1$-blocking agent known as prazosine, hydrazino-phthalazine derivatives, and so on). The increase in the peripheral arterial flow (observed at lower doses) can be advantageous under ischemic conditions; said effect gives just slight changes in the cardiovascular and respiratory parameters.

The employment of diguanido-II is thus advisable, for instance, in the treatment of arterial hypertension caused by an increase in the peripheral vascular resistance ("essential" hypertension, vasculosclerosis, and so on).

We claim:

1. A guanidine derivative selected from the group consisting of members having the following formulas:

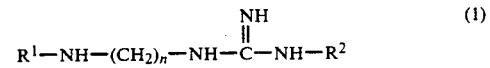

and

-continued

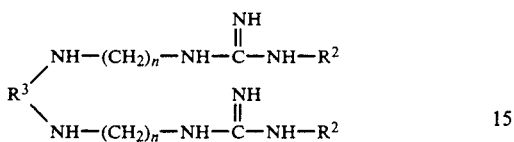

wherein:
R[1] is hydrogen or 3, 4 dimethyoxy cinnamoyl;
R[2] is hydrogen, an alkyl having 1–5 carbon atoms, or an alkenyl having 1–5 carbon atoms with the proviso that R[1] and R[2] cannot both be hydrogen;
$R_3$ is truxinoyl or truxilloyl, each substituted with four methoxy groups in the 3- and 4- positions on the two rings; and,
n is an integer from 1 to 8.

2. A guanidine derivative selected from the group consisting of members having the following formulas:

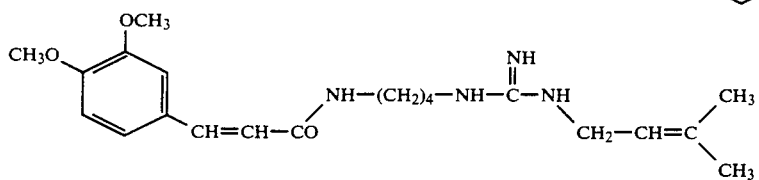

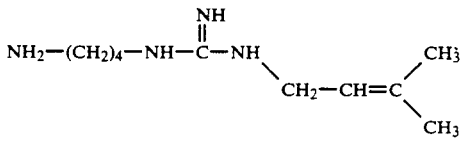

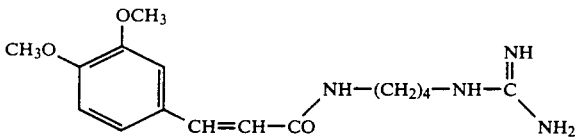

and

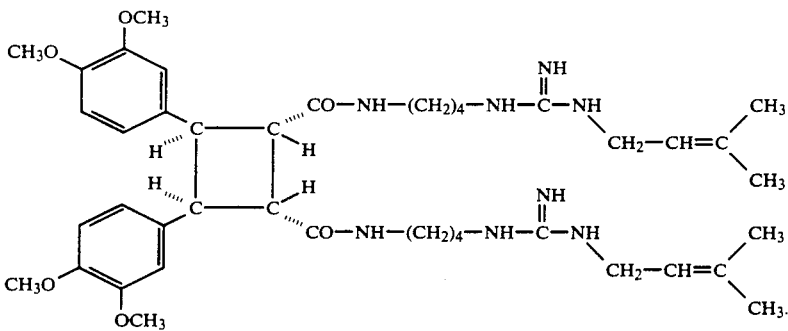

3. Guanidine derivatives according to claim 1, wherein R[2] is prenyl.

4. A guanidine derivative according to claim 2, of the formula:

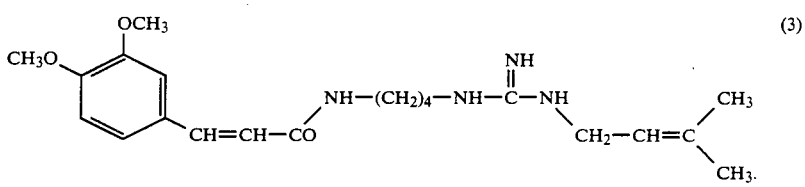

5. A guanidine derivative according to claim 2, of the formula:

$$H_2N-(CH_2)_4-NH-\overset{NH}{\overset{\|}{C}}-NH-CH_2-CH=C\overset{CH_3}{\underset{CH_3}{\diagdown}}$$ (4)

6. A guanidine derivative according to claim 2, of the formula:

(5)

7. A guanidine derivative according to claim 2, of the formula:

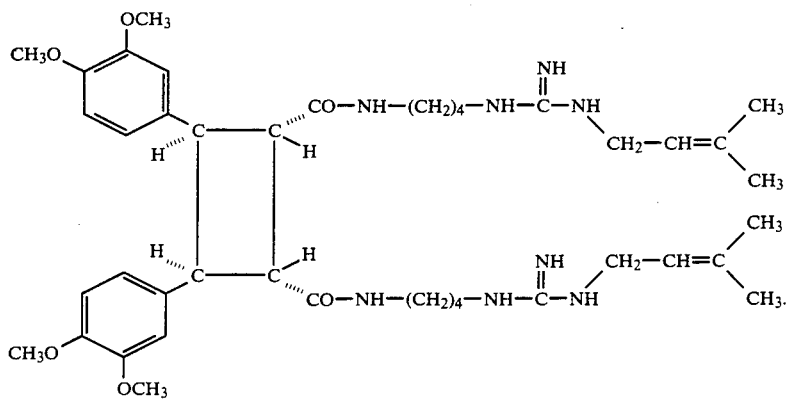
(6)
8. A pharmaceutical composition for treatment of hypertension, comprising an effective amount of one or more compounds as claimed in any of the preceeding claims, in a pharmaceutically acceptable carrier.
* * * * *